United States Patent
Hafez

(10) Patent No.: US 10,966,787 B2
(45) Date of Patent: Apr. 6, 2021

(54) APPARATUS AND SYSTEM FOR ACQUIRING DATA FROM BONES AND JOINTS, PLAN SURGERY AND MANUFACTURE INSTRUMENTS OR IMPLANTS

(71) Applicant: Mahmoud Alm El Din Hafez, Giza (EG)

(72) Inventor: Mahmoud Alm El Din Hafez, Giza (EG)

(*) Notice: Subject to any disclaimer, the term of this patent is extended or adjusted under 35 U.S.C. 154(b) by 215 days.

(21) Appl. No.: 16/096,921

(22) PCT Filed: Apr. 26, 2016

(86) PCT No.: PCT/EG2016/000015
§ 371 (c)(1),
(2) Date: Oct. 26, 2018

(87) PCT Pub. No.: WO2017/186255
PCT Pub. Date: Nov. 2, 2017

(65) Prior Publication Data
US 2019/0201101 A1  Jul. 4, 2019

(51) Int. Cl.
*A61B 34/10* (2016.01)
*G16H 20/40* (2018.01)
(Continued)

(52) U.S. Cl.
CPC ............ *A61B 34/10* (2016.02); *A61B 5/05* (2013.01); *A61B 5/1079* (2013.01); *A61B 8/0875* (2013.01); *A61F 2/30942* (2013.01);
*G16H 20/40* (2018.01); *G16H 30/20* (2018.01); *A61B 2017/00526* (2013.01);
(Continued)

(58) Field of Classification Search
CPC ........................... A61B 34/10; A61F 2/30942
See application file for complete search history.

(56) References Cited

U.S. PATENT DOCUMENTS 9,220,517 B2   12/2015 Lang et al.
2002/0010458 A1 *  1/2002 Urich .................. A61F 9/00745
606/1

(Continued)

FOREIGN PATENT DOCUMENTS

WO     WO2012176077 A1    12/2012

*Primary Examiner* — Andrew Yang
(74) *Attorney, Agent, or Firm* — King & Schickli, PLLC

(57) ABSTRACT

This invention relates to Patient-Specific Templates (PST) which have already been used by implant manufacturers and clinically applied by orthopedic surgeons. This work presents an apparatus comprised of a unit acquiring data from the surface of bones and joints, a computerized unit for surgical planning and a desktop 3D printer for manufacturing PST, which are functionally, physically and electrically connected. The apparatus is compact, portable and suitable for hospital-based or clinic-based service. The data-collection unit has electro-magnetic (EM) device, diagnostic ultrasound machine, laser scanner and a receiver for acquisition of external data. It integrates the data from multiple sources and has sensor fusion ability. The surgical planning unit has specific software program capable of merging the collected data through mathematical model of specific parts of bones, joints and a library of implants and prostheses.

13 Claims, 3 Drawing Sheets

(51) Int. Cl.
*G16H 30/20* (2018.01)
*A61B 5/05* (2021.01)
*A61B 5/107* (2006.01)
*A61B 8/08* (2006.01)
*A61F 2/30* (2006.01)
*A61B 90/00* (2016.01)
*A61B 17/00* (2006.01)
*A61F 2/46* (2006.01)

(52) U.S. Cl.
CPC ... *A61B 2034/108* (2016.02); *A61B 2090/373* (2016.02); *A61B 2090/374* (2016.02); *A61B 2560/0431* (2013.01); *A61F 2002/30948* (2013.01); *A61F 2002/30952* (2013.01); *A61F 2002/30985* (2013.01); *A61F 2002/4663* (2013.01)

(56) References Cited

U.S. PATENT DOCUMENTS

| | | |
|---|---|---|
| 2012/0041446 A1 | 2/2012 | Wong et al. |
| 2014/0200902 A1 | 7/2014 | Aram et al. |

\* cited by examiner

2 - A

2 - B

3 - A    3 - B    3 - C

4 - A    4 - B

APPARATUS AND SYSTEM FOR ACQUIRING DATA FROM BONES AND JOINTS, PLAN SURGERY AND MANUFACTURE INSTRUMENTS OR IMPLANTS

TECHNICAL FIELD

Prostheses and implants are commonly used in bone and joint surgery (orthopaedics). The surgical operations usually require instruments and tools to help the surgeon to implant the prosthesis. Major operations such as joint replacement, spinal surgery and bone tumour surgery are technically demanding. The results of these major surgical operations are dependent on the type of implants and surgical techniques including instruments and tools.

One of the examples for bone and joint surgery is knee replacement. It involves the implantation of the knee prosthesis after sizing the implant and machining (drilling, cutting and/or milling) the joint surfaces to match the internal geometry of the prosthesis. The surgery for knee replacement involves more than 50 surgical steps and usually requires more than 300 pieces of conventional instruments and surgical guides. The aim of knee replacement surgery is to achieve long-term implant survival and successful functional outcome with cost effectiveness and minimal complications. Technical errors can have detrimental effects on function and survival. Component malpositioning may lead to wear and loosening or patellar can cause instability which results in early failure and revision surgery. Computer-assisted robotics and navigation technology have proved to be more accurate than conventional instruments but they have not gained popularity due to several limitations such as complexity of use, high cost and inability to completely replace conventional instruments. Recently, a new technique was introduced to overcome the listed drawbacks. This technique is called "Patient Specific templates (PST)," which is a new concept of utilizing computer-assisted preoperative planning to provide custom-made surgical guides or templates that can work as instruments and partly or completely replace conventional instrumentation systems. This new technique of patient-specific templates (PST) was reported by Hafez et al (1). The same principles have also been used to manufacture patient-specific implants (PSI). PST has been reported to eliminate the use of intramedullary rods of the conventional technique with its concerns of potential blood loss, fat embolism, inaccuracy and infection.

BACKGROUND ART

The concept of patient-specific templates (PST) has already been exploited by all major implant manufacturers. It has been clinically applied on many joints such as knee, hip, shoulder and ankle. The commercially available PST is company-based, where the templates are designed based on specific company implants and cannot be used for any other implants. The preparation is not surgeon-based and it takes long duration for confirming the preoperative planning and fabricating the templates as the company outsources most of the steps of PST process such as planning of surgery and designing of PST. Following template fabrication, the templates return to the company for packing and sterilization. Finally, the company sends the templates to the hospital, so that the surgeon can use during surgery. The process does not only involve outsourcing the steps but it also involves more than one country. Planning is routinely done by technicians and not by surgeons as both usually work at different locations. In addition, medico-legal experts described PST as a complex process and surgeons who do not plan or design PST still have responsibility toward its failure. Furthermore, companies should not manufacture PST without achieving an approval from the surgeon, which has to be done online. The required delivery and transportation from one place to another make the logistics for this technique a bit more complex. The process of PST takes about 4-6 weeks from the time of acquiring the imaging (MRI or CT) until the templates are delivered to the hospital. This may carry the risk of anatomic changes to the knee as a result of daily activities or any abnormal loading during this long delay, resulting in intraoperative malpositioning of the templates and subsequently implant malalignment.

This complex process and logistics limit the availability of PST in developing countries where implant companies are not widely distributed. The surgeons usually need longer time for communication with implant manufacturers to obtain the custom cutting guides and the desired implant. There is an additional high cost for the process of PST that is not proven to be cost effective [3, 4].

In the current art, the data collection is not sophisticated and it comes from one imaging machine (CT or MRI). MRI has the theoretical advantages of detecting cartilage and being a radiation-free imaging. However, CT scan is easier to use owing to the limitations of MRI such as difficult segmentation, contraindications with the presence of pacemaker, implants and obesity. Its other limitations, which have a different magnitude according to different health care systems, are cost, long waiting list, reimbursement and other logistics. CT-based software systems are easier to use, as image segmentation can be done automatically. On the other hand, MRI-based systems have to be done by experienced technicians due to the need to perform manual segmentation of the images. The malpositioning of the templates can occur as a consequence of incorrect bone segmentation with MRI. It is worth mentioning that the availability of good MRI or CT-scan machines is not always guaranteed in developing countries. In addition to the drawbacks of CT and MRI, both involve additional procedure, time and cost. This imposes another limitation to the wide spread of PST or PSI. There have been attempts to convert 2D X-ray data into 3D images but these trials lacked accuracy and are not reliable for producing patient-specific templates or implants.

The expensive industrial rapid prototyping (RP) machines that are used to manufacture PST have an average cost of $500,000. But currently the availability and affordability (<$500) of desktop 3D printers make it possible to replace the industrial RP machines. One of our patents described an open-platform technique (4), where the PST is designed and manufactured for any available knee implants or any implants that can be introduced in future. Using the open-platform technique, it is possible to use PST in developing countries, where there are implants from companies that have no PST technology or low-cost implants.

However, other problems still exist with the currently commercially available PST and even the open-platform technique. These problems are the outsourcing of different steps of PST process or the need for using different machines and devices even if they are in one location.

In the current art, at least 3 processes (data collection, planning of surgery and production of PST or PSI materials) are managed by 3 different companies, possibly in 3 different countries. None of these PST or PSI systems has been reported as a hospital-based procedure.

However, the model of hospital-based health care system is not new. Literature showed several benefits of hospital-based health-care systems (2). As hospitals routinely have a high number of physicians in different specialties, this could be important predictor for quality and cost of care; and consolidation of such different specialties contributes further for better quality-of-care environment. Moreover, promoting health-care system integration while providing risk sharing could also decrease the expenses of procedures, imaging and tests while improving the quality of care.

Hospital-based health-care services should be provided in public and academic hospitals with clinical, administration and economic staff who are capable of undertaking clinical practice, administrative decision making, assessment of apparatus and procedures, examining the effectiveness, safety and cost data as well as organizing training workshops, seminars, learning courses and collaborative networks.

Our patents cover a range of different devices and methods for PST and PSI. One of our patents described a new concept and application of double joint line for use in patient specific implants (4) Another one described a tool for PST and PSI for canine and have been applied on dogs (5). Also, a patent described coupling techniques for connecting PST to conventional instruments (6).

REFERENCES

1. Hafez M A, Chelule K, Seedhom B B, Sherman K P. Computer-assisted total knee arthroplasty using patient-specific templating. Clinical Orthopaedic and Related Research. 2006; 444:184-192
2. Craig A. Umscheid, Kendal Williams and Patrick J. Brennan. Hospital-Based Comparative Effectiveness Centers: Translating Research into Practice to Improve the Quality, Safety and Value of Patient Care. J Gen Intern Med. 2010.
3. Patient specific instruments and related methods for joint replacement. U.S. 61/641,851.
4. A Device and A Technique of Patient Specific Instruments for Knee Arthroplasty With A Universal and An Open Platform. PCT/EG2013/000014.
5. A Tool For Custom-Made Instruments And Implant For Artificial Knee Joint Of Dogs. PCT/EG2015/000004.
6. A Method for Connecting Custom-made Guides to Conventional Instruments for Joint Replacement. PCT/EG2015/000013.

DESCRIPTION OF INVENTION

This is an apparatus for acquiring data from the surface of bones and joints, surgical planning and manufacturing PST or PSI. The apparatus comprises of 3 units: a data collection unit, a computerized unit and a desktop 3D printer. These units are functionally, physically and electrically connected. The apparatus is compact, portable and suitable for hospital-based or clinic-based service. The apparatus has a data-collection unit that comprises of 4 components: electro-magnetic (EM) device, diagnostic ultrasound machine, laser scanner and a receiver for acquisition of external data. These components are physically and electrically connected and function as one unit. The said unit integrates the data from multiple sources and has sensor fusion ability.

This invention is meant to overcome all shortfalls of the currently available PST or PSI mainly the outsourcing of different steps of the procedures or the need to use different devices and programs. Using this system, the main steps of PST/PSI, that is, data collection, planning of surgery, production of PST/PSI are done in one apparatus, thus the system is used as a hospital-based or clinic-based. The whole procedure of hospital-based PST/PSI can be performed in one place under the surgeon control and the average time needed for imaging, planning and fabrication of templates can be cut short to few days.

The invention is an apparatus and method for acquiring data from bones and joints of an individual, integrating and reconstructing data, then planning the surgery and manufacturing PST/PSI based on these data. It has 3 units that are functionally integrated and connected physically and electrically. Finally, the integration of all 3 units in a compact portable apparatus provides a unique function that did not exist before (hospital-based service). In this patent, the data collection is unique as it comes from different sources and are integrated to formulate a complete dataset.

This hospital-based PST technique does not require a company representative for transferring data, radiographs or documents; thus, the technique seems suitable for countries that are out of the scope of implant companies' interests. In this hospital-based system, imaging, planning, sizing, designing and production of PST are done by one portable machine that is located in the hospital or even in outpatient clinics. The overall procedure is done under direct supervision of the surgeons or by the surgeon himself. The communication is swift and easy, and direct feedback can be given by the surgeon to adjust the plan to the optimally desired design.

The material used for the production of PST in this hospital-based PST was nylon, which meets certain criteria such as being biocompatible, heat stable to withstand high temperature of sterilization, durable enough not to be damaged by saw blades and relatively inexpensive. In addition, it is easily manufactured within a short period of time. ABS and polycarbonate are other plastic materials that can be produced and used for PST. They are sterilized by Gamma radiation, ethylene oxide or plasma. PEEK can be produced by the desktop 3D printer and it is suitable for PSI.

Once the operation is planned and the PST or PSI are fabricated, the surgery is performed at the same hospital.

For planning, there is a special program (OrthoNovi), which has information about the implant to be used in the form of three-dimensional CAD files of different sizes. It also, has a mathematical model of relevant bone and joints. The program reconstructs images from the collected data and displays them on the computer screen as a 3D model.

The anatomy of the bone and joint is created and displayed in three dimensions (coronal, sagittal and transverse planes), with the ability to rotate and tilt the images to view all its aspects (front, back and sides) at any angle.

Default planning was based on the standard parameters, such as 3 degrees of external rotation for the posterior femoral cut and 0 degrees for coronal tibial cut. The surgeon's preference could be added to the default, such as 5 degrees of posterior slope in the tibial cut. The default settings could be changed according to the specific nature of the case or the surgeon's preference. Sizing of the femoral and tibial components was done automatically by the system and verified to avoid undue anteroposterior and mediolateral mismatching or any implant overhang in any plane. The planning could reveal information that would not be available to the surgeon during actual surgery, such as posterior tibial overhang or posterior femoral offset.

Alignment (angles and rotation) and bone resection were planned according to the set default for eight standard parameters: femoral coronal alignment, femoral sagittal alignment, femoral rotation, level of distal femoral cutting, tibial coronal alignment, tibial sagittal alignment, tibial rotation and level of tibial cutting (6). The ideal bone cuts were measured on software with definite length, direction and inclination (6).

Surgeons have a major role in preoperative planning, either by performing the planning on the software or by supervising the technician, which increases the accuracy of planning and shortens the time of the whole process. In this hospital, we have a specialized team of engineers for more efficient preoperative planning, and direct communication with the surgeon, being also responsible for the fabrication of PST inside the hospital. Designing of patient specific implants is possible at this stage if needed. The final design of the PST was transferred electronically to the production unit that manufacture d the physical templates or implants. Desktop 3D printers are used for this purpose.

The patient's initials along with the side and size of the knee implant were printed on the templates, and packing was done in special packs. The final cutting guides could thus be used for a specific patient, and the surgeon could finally do the operation using these templates.

Hospital-based PST/PSI is a practical and time-saving system. The procedure has proven feasible and easy. Planning was controlled by the surgeon. PST/PSI production is done by desktop 3D printers which are less expensive than industrial rapid prototyping machines.

The machine was designed to be an integrated system have three units for data collection, planning and 3D printing. These three units was created in a direct connection to each other.

Figure 1:
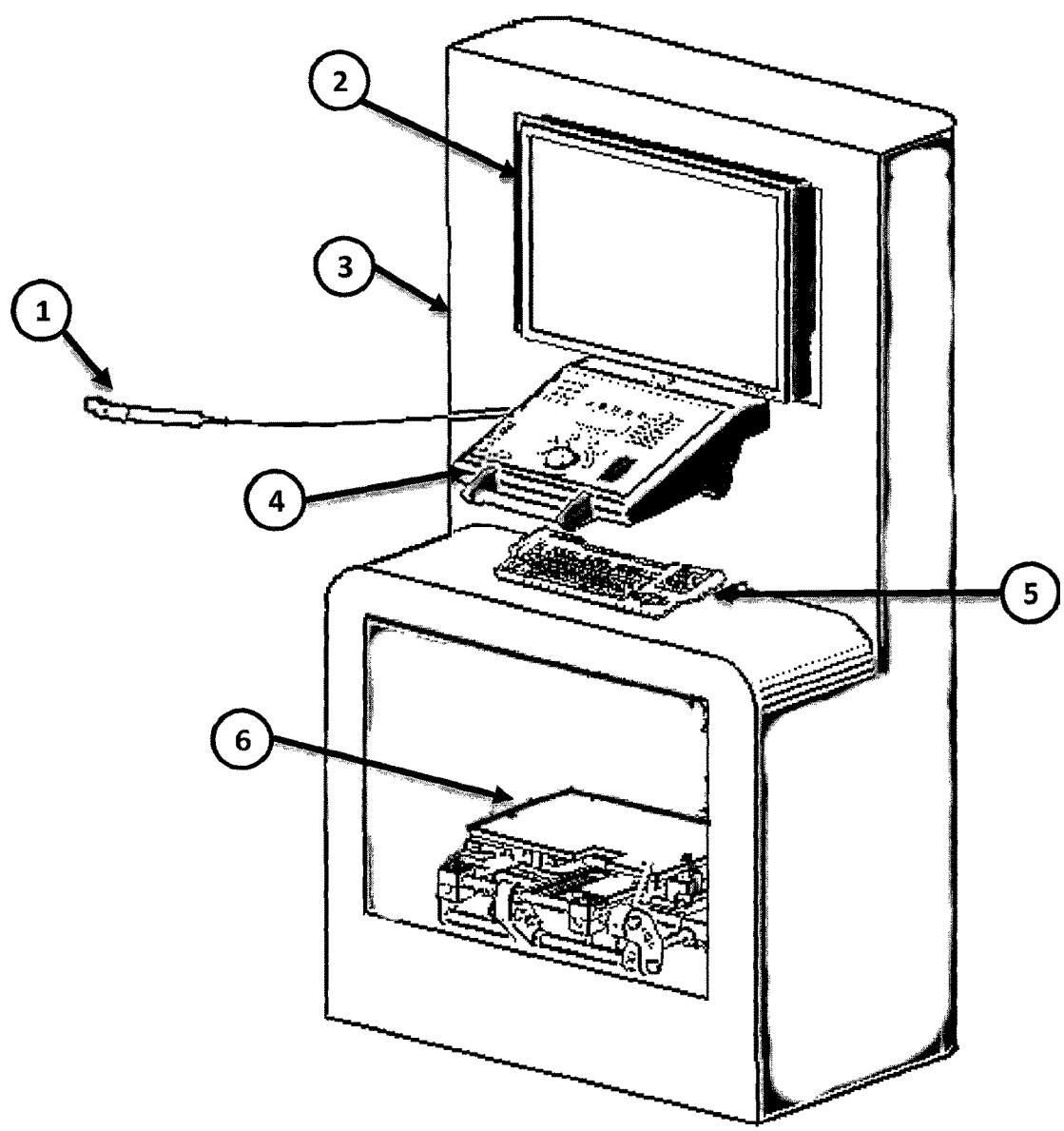
FIG. 1: Hospital Based Machine

The data collection unit (FIG. 1) was designed to acquiring data from bones and jointed based one ultrasound probe, laser scanner and electromagnetic probe (FIG. 1). Attached PC have a specific medical software to perform planning of surgery (FIG. 1). Output unit is a 3D printing device directly connected to PC and have a feedback unit to recover machine operating errors (FIG. 1)

Figure 2:
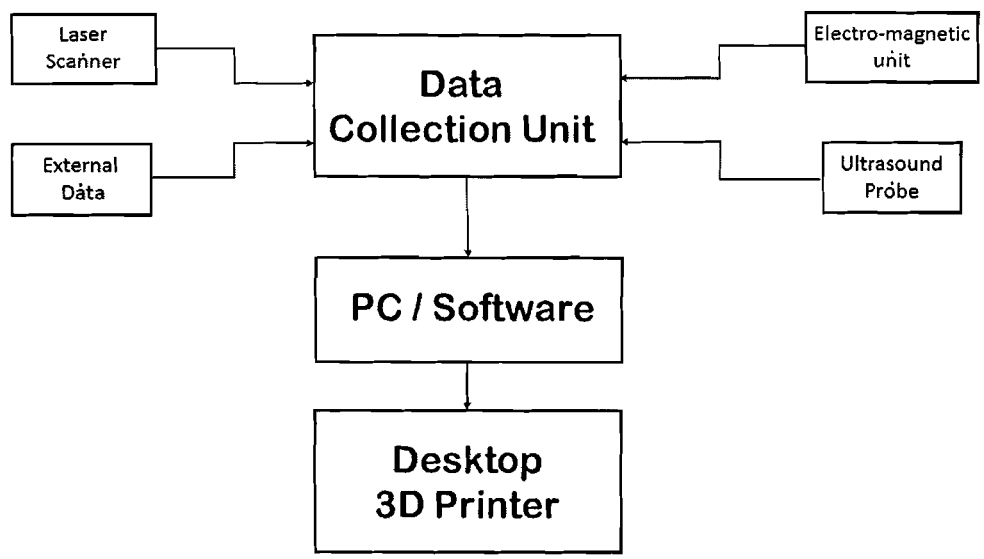
Figure 2:
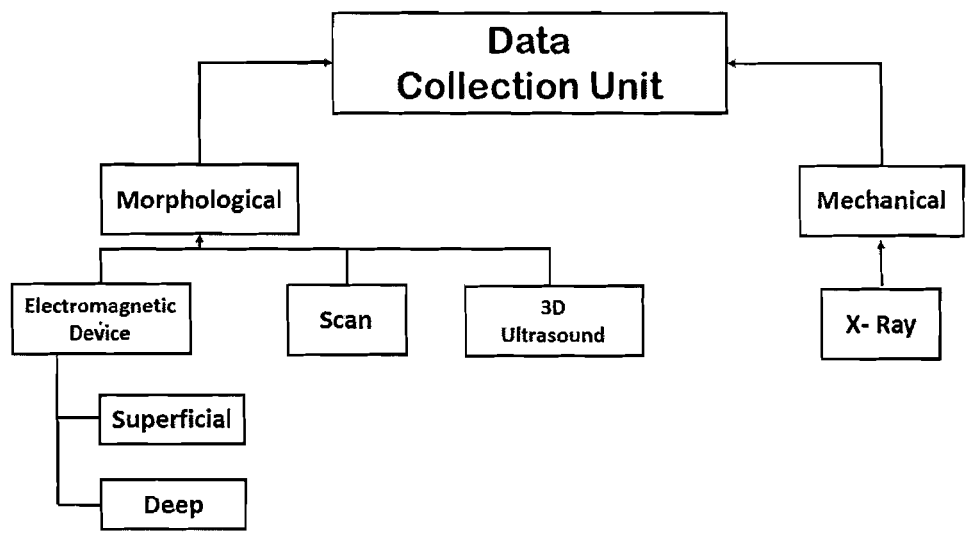

FIG. 2: Hospital Based Machine Concept

A chart in (FIG. 2) describe the processing of hospital based machine starting from the data collected from multiple source as laser scanner, electromagnetic probe and ultrasound probe (FIG. 2-B). Transferring the collected data to specific medical software to perform surgery planning (FIG. 2-A). A desktop 3D printer automatically receives the final design of instruments or implants and produce it based on various 3D printing technologies supplied with biocompatible materials (FIG. 2-A).

Figure 3:
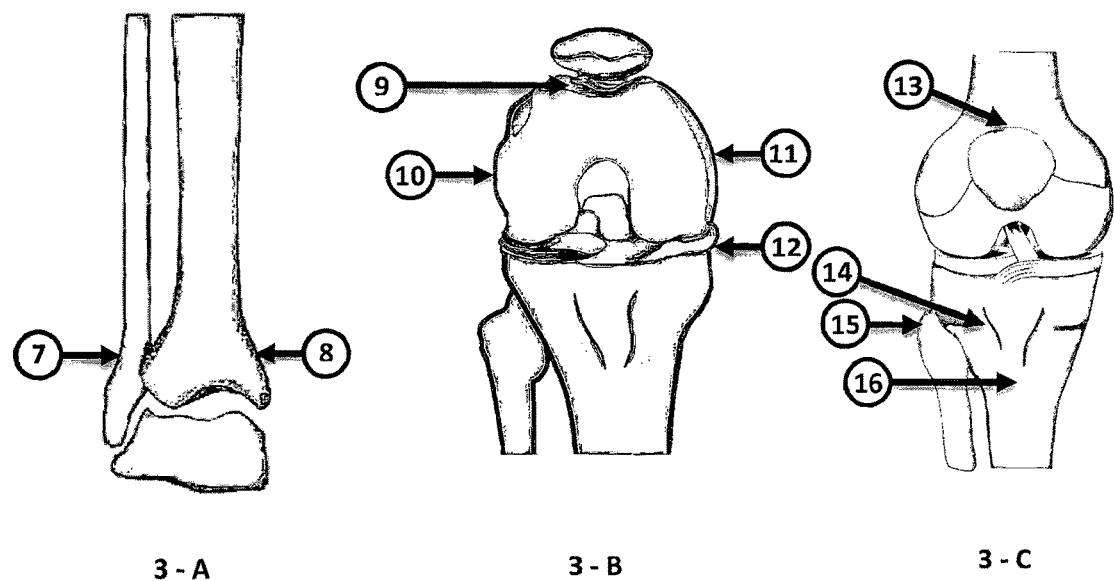

FIG. 3: Knee Surface Anatomy

Data collection unit was designed to perform surface scanning depends on landmarks and surface anatomy of bone and joints. Scanning was created externally across the skin and percutaneously. The landmarks include all identifiable bone and soft tissue structures such as bone prominence, tendons.

Figure 4:
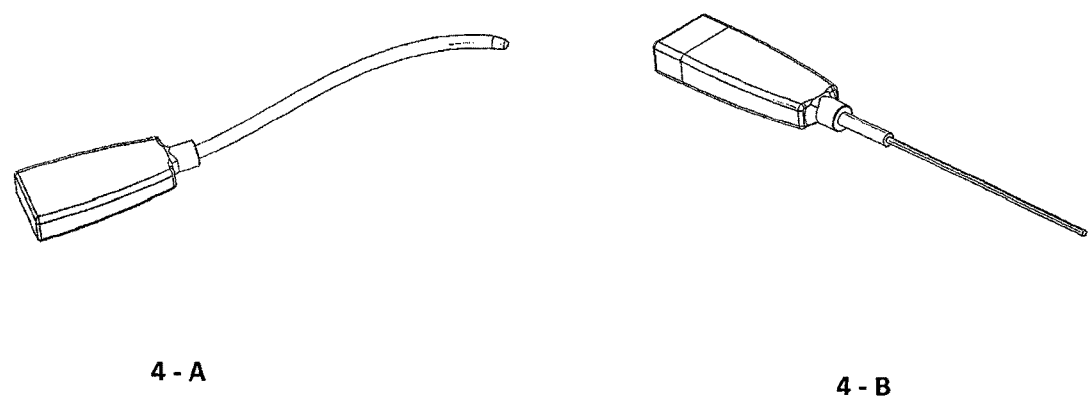

FIG. 4-A and 4-B: Electromagnetic Probe

Two types of probes are used to preform detection of landmarks as a superficial (FIG. 4-A) and deep pin (FIG. 4-B)

DRAWING LABELS

1. US Probe
2. Monitor
3. Machine Body
4. US panel
5. Software Controller
6. Embedded 3D printer
7. Superficial landmark
8. Deep landmark
9. Upper pole patella
10. Lateral epicondyle eminence
11. Medial epicondyle eminence
12. Upper end tibia
13. Upper pole patella
14. Tibial tuberosity
15. Fibula head
16. Tibia shin

The invention claimed is:

1. A system for acquiring data from the surface of bones and joints for surgical planning and manufacturing of patient-specific templates and patient specific instruments using an apparatus comprised of three units: a data collection unit, a computerized unit and a desktop 3D printer, which are functionally, physically and electrically connected to each other in a compact, portable fashion and suitable for hospital-based or clinic-based service, wherein:
   the data-collection unit comprises four components: an electro-magnetic (EM) device, a diagnostic ultrasound machine, a laser scanner and a receiver for acquisition of external data, which are physically and electrically connected and function as one unit that integrates the data from multiple sources and has sensor fusion ability; and
   the apparatus further comprises a compatible diagnostic 3D ultrasound (US) machine and its software with musculoskeletal probe, said US machine being designed to complement the other three components in the data-collection unit in order to formulate a complete dataset for the area of interest of bones and joints.

2. The system according to claim 1, wherein the apparatus has an EM device to collect data based on landmarks and surface anatomy of bone and joints either superficially over the skin through a probe or internally through a percutaneous fine pin, which is designed to complement the other three components in the data collection unit in order to formulate a complete dataset for the area of interest of bones and joints.

3. The system according to claim 2, wherein the apparatus comprises a 3D camera and/or laser scanner to collect data about the contour and the morphology of bones and joints, the 3D camera being designed to complement the other three components in the data collection unit in order to formulate a complete dataset for the area of interest of bones and joints.

4. The system according to claim 1, wherein the computerized unit comprises specific software program capable of merging the collected data, which has a mathematical model of specific parts of bones and joints and a computer-readable medium having a program to perform the complete surgery with a built-in library of implants and prostheses for the relevant surgeries on bones and joints.

5. The system according to claim 1, wherein the desktop 3D printer is connected to and compatible with the other two units, and automatically receives the final computer-aided design of instruments or implants and manufactures biocompatible materials using the technology of FDM, SLA or SLS.

6. The system according to claim 1, wherein the system has a data-collection process that integrates data coming from multiple sources: EM device, ultrasound machine, laser scanner and external data, where the four components complement each other to provide a complete dataset for the area of interest of bones and joints having the ability to reverse engineering the bones and joints using integrated data from multiple sources instead of CT or MRI and functioning as a visualization system by converting 2D data to 3D images within the XYZ coordinates.

7. The system according to claim 6, wherein the system has an EM process designed to collect data from landmarks and surface anatomy of bones and joints, the landmarks including all identifiable bone and soft tissue structures such as bone prominence, tendons, ligaments, vessels, joint surface and soft spots.

8. The system according to claim 7, wherein the system is designed to perform a process of data collection from musculoskeletal 3D US probe in the form of video, images and numerical data which collect data from the surface of bone through a panoramic scanning around the contour of bone and joints.

9. The system according to claim 7, wherein the collected data are imported by the computerized unit and converted to numerical data compatible to the process of planning surgery.

10. The system according to claim 6, wherein the system comprises a receiver to acquire external data such as 2D X-ray images, in DICOM or other formats, and other patient-specific data such as age, height, weight, degree of deformity of the bones and range of motion of joints.

11. The system according to claim 6, wherein the X-ray data include the long axes of bones, namely mechanical and anatomical axes, while the receiver reconstructs and converts this format to compatible data that are accepted by the planning software program.

12. The system according to claim 6, wherein the system has a computerized planning process through specific software capable of merging the collected data: reconstructing 3D model and keeping XYZ coordinates, which are superimposed over the mathematical model to create a patient-specific 3D imaging of specific parts of bone and joints, characterized by the ability to directly import 3D data from CT or MRI images and plan surgery on the data while maintaining the XYZ coordinates.

13. The system according to claim 1, wherein the computerized unit includes a computer readable medium having a program to perform the complete surgery, which involves sizing, bone cutting and complete simulation of surgery and designing of instruments and implants.

* * * * *